United States Patent [19]

Tuttle et al.

[11] Patent Number: 5,395,970
[45] Date of Patent: Mar. 7, 1995

[54] 1-(3,4-DIHYDROXYPHENYL)-2-(4-(4-HYDROXYPHENYL)BUTAYLAMINO)ETHANOL

[75] Inventors: Ronald R. Tuttle, Escondido; Clinton E. Browne, III, Oceanside, both of Calif.

[73] Assignee: Gensia Pharmaceuticals, Inc., San Diego, Calif.

[21] Appl. No.: 169,536

[22] Filed: Dec. 15, 1993

Related U.S. Application Data

[60] Continuation of Ser. No. 20,228, Feb. 19, 1993, abandoned, which is a continuation of Ser. No. 833,645, Feb. 10, 1992, abandoned, which is a continuation of Ser. No. 625,482, Dec. 11, 1990, abandoned, which is a division of Ser. No. 308,683, Feb. 9, 1989, Pat. No. 5,108,363, which is a continuation-in-part of Ser. No. 157,875, Feb. 19, 1988, abandoned.

[51] Int. Cl.$^6$ .................................... C07C 215/60
[52] U.S. Cl. .................................... 564/361; 564/165
[58] Field of Search ........................ 564/165, 361

[56] References Cited

U.S. PATENT DOCUMENTS

| | | | |
|---|---|---|---|
| 3,135,797 | 6/1964 | Biel | 564/361 |
| 3,952,021 | 4/1976 | Ikezaki et al. | 564/361 |
| 4,460,580 | 7/1984 | Ostermayer et al. | 564/165 |
| 4,478,849 | 10/1984 | Ainsworth et al. | 564/165 |
| 4,845,127 | 7/1989 | Mills et al. | 564/165 |

FOREIGN PATENT DOCUMENTS 0570892 2/1959 Canada ........................ 564/361

OTHER PUBLICATIONS

Philip's, Chemical Abstracts, vol. 52 (1958) 15578g.
Külz, Chemical Abstracts, vol. 3 (1959) 10130a–b.
Biel, Chemical Abstracts, vol. 54 (1960) 1441g.
Ariens et al, Chemical Abstracts, vol. 55 (1961) 9666e.

*Primary Examiner*—Richard L. Raymond
*Attorney, Agent, or Firm*—Lyon & Lyon

[57] ABSTRACT

Methods and devices for the diagnosis, evaluation and treatment of coronary artery disease (CAD) by means of a closed-loop drug delivery system that delivers an exercise simulating agent, including novel exercise simulating agents which elicit both acute and adaptive cardiovascular responses similar to those elicited by aerobic activity are provided. The acute responses to the exercise simulating agent are used to diagnose and evaluate CAD in lieu of the acute responses to aerobic exercise. Due to their adaptive responses these compounds may be used to treat CAD in lieu of the adaptive responses caused by aerobic exercise training or to treat other conditions where the adaptive responses caused by aerobic exercise are desirable.

2 Claims, 2 Drawing Sheets

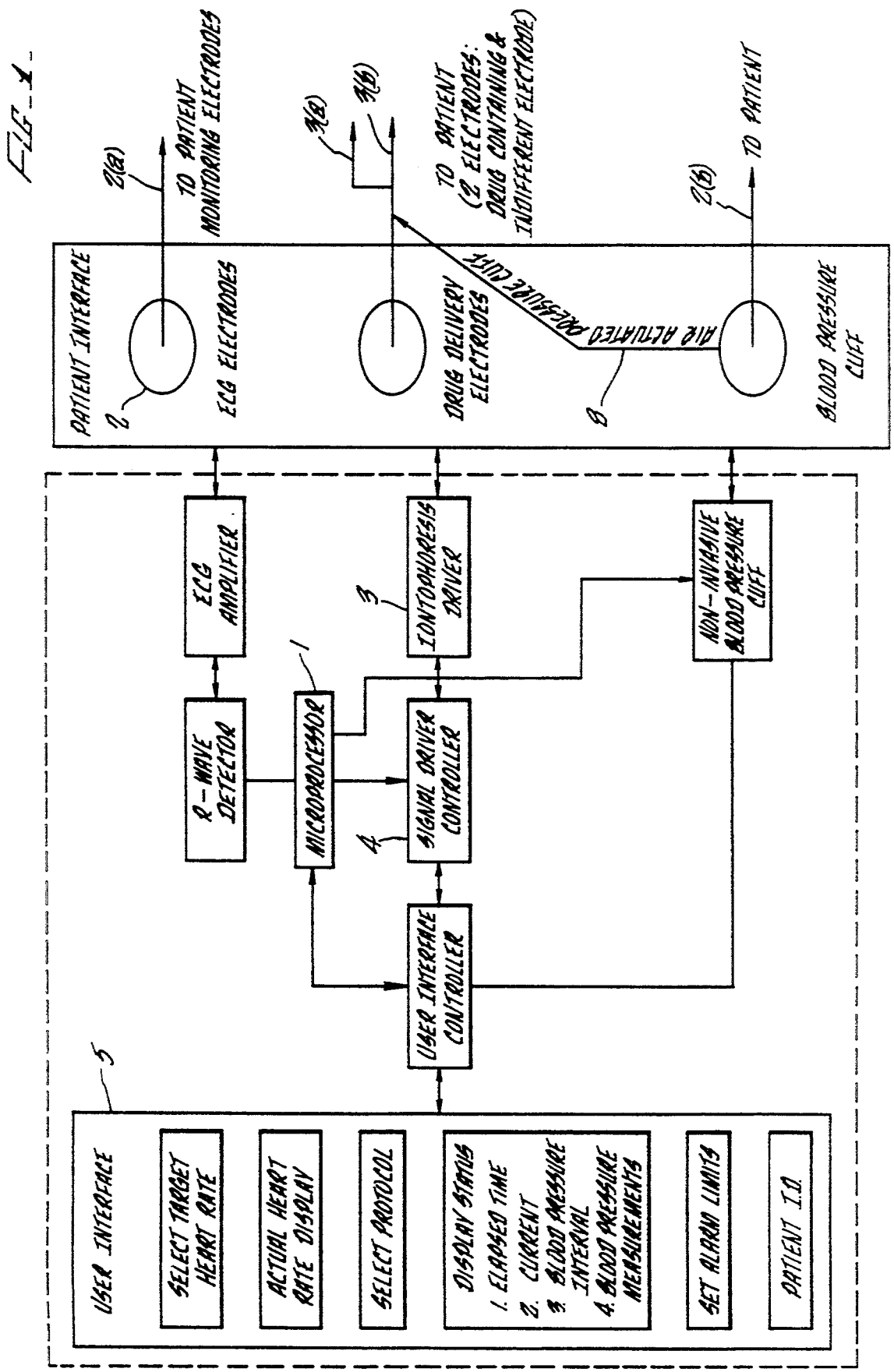

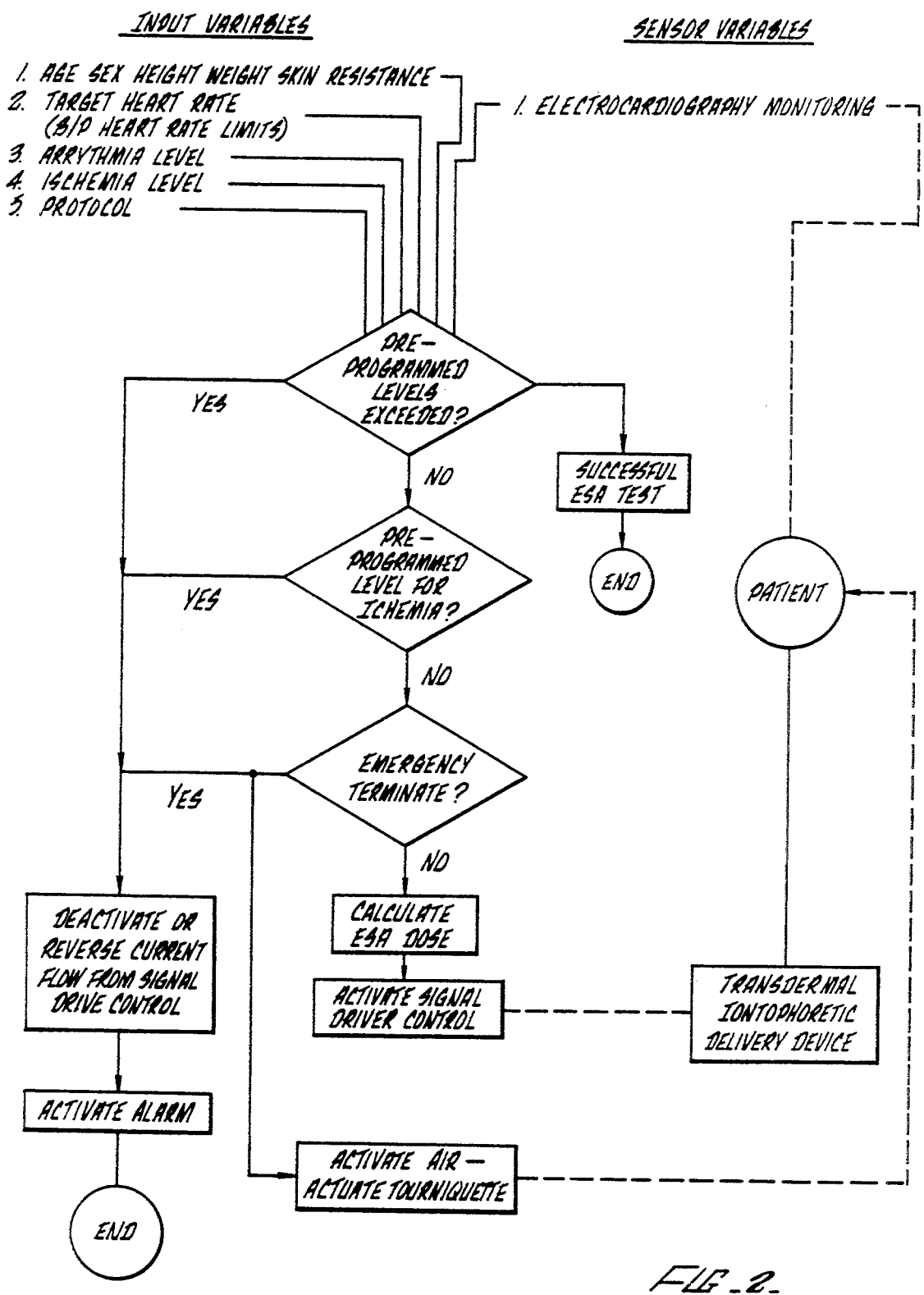
FIG_2

1-(3,4-DIHYDROXYPHENYL)-2-(4-(4-HYDROXY-PHENYL)BUTAYLAMINO)ETHANOL

CROSS REFERENCE TO RELATED APPLICATIONS

This application is a continuation of application Ser. No. 08/020,228, filed Feb. 19, 1993, now abandoned, which is a continuation of application Ser. No. 07/833,645, filed Feb. 10, 1992, now abandoned, which is a continuation of application Ser. No. 07/625,482, filed on Dec. 11, 1990, now abandoned, which is a divisional of application Ser. No. 308,683, filed on Feb. 9, 1989, now U.S. Pat. No. 5,108,363, which is a continuation-in-part Ser. No. 157,875, filed Feb. 19, 1988, now abandoned.

FIELD OF THE INVENTION

The invention relates generally to the diagnosis, evaluation and treatment of coronary artery disease and more specifically to a system for closed loop delivery of a exercise simulating agent, said exercise simulating agent eliciting both acute and adaptive cardiovascular responses similar to those resulting from aerobic activity. The present invention is also directed to novel exercise stimulating agents and to therapeutic agents having both acute and adaptive cardiovascular and metabolic effects.

BACKGROUND AND INTRODUCTION TO THE INVENTION

Publications and other reference materials referred herein are incorporated herein by reference and are numerically referenced in the following text and respectively grouped in the appended Bibliography which immediately precedes the claims.

The drugs described and claimed herein that elicit acute and adaptive cardiovascular responses similar to the types of responses elicited by aerobic activity are referred to as Exercise Simulating Agent Beta Agonists (hereinafter "exercise simulating agents" or "ESA ™ beta agonists") for the purposes of this invention. While eliciting such cardiovascular responses, it has been discovered that the effects of administration of ESA ™ beta agonists can be finely controlled so that the heart is exercised or stressed .at selected levels without body motion.

According to the American Heart Association, heart disease, stroke and related disorders accounted for nearly one million deaths in 1984, almost as many deaths as from all other causes of deaths combined. Cardiovascular and cerebrovascular diseases affect over 63 million people in the United States, equivalent to one of every four Americans. Approximately 5 million people in the United States suffer from coronary artery disease (hereinafter "CAD"), resulting in over 1.5 million heart attacks yearly, of which 550,000 are fatal. The annual economic cost of cardiovascular disease alone is estimated to be $85 billion. Cardiovascular disease has many manifestations, of course, including atherosclerosis.

Atherosclerosis is the most common form of arteriosclerosis, commonly referred to as "hardening of the arteries." Atherosclerosis is a degenerative process that narrows or blocks arteries in the heart, brain and other parts of the body; the interior walls of the arteries become lined with deposits of fat, cholesterol, fibrin, cellular waste products and calcium. These deposits form a rough, thick surface inside the blood vessels, and interfere with both the smooth flow of blood and the amount of blood carried through the arteries. This narrowing of the blood vessels restricts blood flow, causing ischemia (deficiency of blood due to either functional constrictions or obstruction of a blood vessel), and is the underlying pathologic condition in many forms of cardiovascular disease including CAD, aortic aneurysm, peripheral vascular disease and stroke. In the majority of cases, the first indication of atherosclerosis is seen during exercise when the oxygen requirement of the heart muscle (myocardium) increases.

Indeed, atherosclerosis is generally silent until it manifests itself as CAD, peripheral vascular disease, stroke, or sudden death. There are essentially no easy, rapid or economic tests to detect the presence of atherosclerosis before it is clinically evident, and the only treatment for it is the modification of risk factors (i.e., cigarette smoking, high blood pressure, blood cholesterol and diabetes) once atherosclerosis is detected in an asymptomatic individual.

Disorders of the coronary arteries are common manifestations of atherosclerosis. CAD develops when the coronary circulation is insufficient to supply the oxygen requirements of the heart muscle, resulting in ischemia. CAD has three major clinical manifestations: angina pectoris, a condition marked by periodic episodes of chest pain, especially during exertion, that result from transient and reversible myocardial ischemia (when CAD has progressed such that it is clinically apparent, it is also referred to as ischemic heart disease); myocardial infarction, the term used to describe acute necrotic changes in the myocardium that are usually secondary to coronary occlusion (heart attacks); and sudden death, an unexpected cardiac death occurring within an hour of the onset of the heart attack, often without symptoms. CAD is clearly a diagnostic challenge to the practicing physician because it is often silent and because of the severe consequences of its clinical course.

Several developments in the diagnosis of CAD have taken place in the past 15 or so years. Prior to 1970, the principal techniques available for the evaluation of the patient with heart disease were the clinical examination, the chest x-ray, and electrocardiography (hereinafter "ECG"). If these various modalities were inadequate and clinical symptoms were present, patients were often and in many cases still are subjected to the invasive techniques of cardiac catherization, selective angiography, or both, with the resultant discomfort, risk and necessity for hospitalization. Patients who were diagnosed with CAD usually received clinical examination supplemented by the relatively inaccurate chest x-ray and ECG. The introduction of other noninvasive techniques such as ECG coupled with an exercise stress test ("EST"), ambulatory monitoring electrocardiography and various forms of radionuclide imaging, have improved the diagnosis and management of heart disease, but these techniques are not without serious drawbacks. The value of the noninvasive techniques are limited by the selection of the appropriate diagnostic procedure or procedures, the skill and expertise of the individual(s) performing the procedure, the ability of the patient to successfully tolerate and complete the test, the proper interpretation of the results and the cost and availability of specialized equipment.

Of the above-mentioned noninvasive techniques, exercise stress testing with electrocardiography monitoring is one of the most commonly used tests in the diagnosis of CAD in the United States. Clinical experience has repeatedly confirmed the value of EST in the diagnosis of symptomatic cardiac conditions which are not present at rest but is present under conditions of cardiac stress. At rest the heart may perform adequately and meet the body's requirements for oxygen and other nutrients, but when the heart is stressed with exercise, CAD is more readily detected. The cardiac changes elicited by stress include: (1) increased heart rate; (2) increased cardiac output; (3) increased stroke volume due to increased venous return and increased myocardial contractility; and (4) rise in systolic blood pressure. These changes increase the heart's need for oxygen, and therefore increase the need for coronary blood flow, creating a diagnostically revealing response for detection of CAD.

Exercise stress testing is performed after a baseline resting ECG is taken. The patient is then closely monitored through a protocol of sequential levels of exercise. The Bruce protocol is the most common protocol used in the United States. This protocol specifies the speed and level of the incline of a motor driven treadmill during a total of seven three-minute exercise states with no rest periods. The test is stopped when any of the following occur: when the protocol is completed; when the patient reaches a pre-set heart rate goal; when the patient experiences acute discomfort; when a diagnostic change occurs in the EGG or blood pressure; or when the patient fatigues.

Despite the fact that exercise stress testing is an important method for the diagnosis of CAD, there are drawbacks which limit its overall usage. A significant problem with the procedure is that exercise must be maximal in order to obtain the greatest sensitivity. In other words, for a test to be considered diagnostically revealing, either the patient must reach a level of stress that causes ischemia, or the patient must complete the protocol by reaching a predetermined maximal heart rate. A large group of patients in the target group are physically unable to exercise at all, or are unable to achieve a maximal test due to problems such as arthritis, limb abnormalities, obesity and other conditions. Other problems are related to the use of this technique, including the fact that exercise stress testing is inconvenient to both patient and doctor. A maximal stress test exhausts most patients and involves a significant recovery time. Additionally, maximal stress tests involve a degree of risk for the patient of falling which is directly related to the use of a treadmill. Because of the physical movement associated with the exercise, placement of the electrodes is also a problem. Specially designed electrodes which minimize motion artifacts, must be securely attached. Placing the electrodes can involve shaving of the chest in man, and sometimes burnishing of the skin to achieve appropriate electrode contact. Taken as a whole, those necessities make exercise stress testing an inconvenient test for both patient and physician. Because of its inherent difficulty, lack of sensitivity, lack of specificity, and cost, exercise stress testing is not generally recommended for asymptomatic individuals (1).

Diagnosis of CAD by methods which can stress the heart in a manner that mimics aerobic activity, while not forcing the patient to engage in such strenuous activities would vitiate many of the problems associated with diagnosis of CAD by means of exercise stress testing. In fact, a test wherein the heart is stressed without the need for physical exercise would be not only of great practicality, but would also allow for the testing of those individuals who heretofore have been unable to engage in exercise stress testing.

Several groups have described the intravenous infusion of synthetic catecholamines (2, 3, 4, 5). U.S. Pat. No. 3,987,200 entitled "Method for Increasing Cardiac Contractility" issued to Tuttle et al. on Oct. 19, 1976, discloses the synthetic catecholamine dobutamine. Dobutamine elicits certain specific cardiac responses without the adverse side effects that would accompany administration of a natural catecholamine. Dobutamine exerts a positive inotropic effect (increasing heart contractility) without inducing arrhythmia and with minimal heart rate and blood pressure effects. When infused intravenously at high doses, dobutamine elicits increases in heart rate, myocardial contractility, arterial blood pressure, and coronary and skeletal muscle blood flow. Such responses resemble the effects of physical exercise. Although heart rate does increase with infusion of dobutamine, the drug was designed to specifically minimize this effect. Increasing heart rate is referred to a positive chronotropic effect.

Since the development of dobutamine, there have been reports in the scientific literature on the relationship of dobutamine and physical training (6). Results from studies utilizing dobutamine in the diagnosis of CAD (7, 8, 9) indicate that dobutamine infusion may be a reasonable, well-tolerated cardiovascular stress test used with the various diagnostic modalities. Use of dobutamine as an ESA TM beta agonist for adaptive response purposes has also been reported (10, 11, 12, 13, 14, 15). However, and despite the fact that dobutamine elicits the cardiovascular responses normally associated with exercise, the use of dobutamine has been limited because the drug must be intravenously infused due to its relatively low potency, thus creating additional time and complications for both patient and physician.

Dobutamine has also been administered to prevent bedrest induced physical deconditioning, and it was reported that infusions of dobutamine could maintain or increase many of the physiologic expressions associated with physical conditioning. (16). The use of portable infusion pumps for the administration of dobutamine raised the possibility of overcoming the necessity for hospital confinement, allowing for somewhat ambulatory movement (17, 18, 19, 20). Use of such a system in an outpatient setting for general diagnosis and treatment purposes is of course negated by the need for an attached catheter to the patient. The need for oral inotropic agents to replace this form of therapy has been noted (17, 19). An oral agent, however, while perhaps potentially useful for therapeutic application would not be useful diagnostically, due to the need for fine control of the cardiac response of the drug. For diagnostic purposes, it would be desirable to be able to obtain specific cardiac response over a defined period of time, and to be able to reverse or reduce the effect simply and rapidly.

An orally effective compound, "KM-13", obtained from a specific alteration of dobutamine's chemical structure was recently discussed (21) and is the subject of a United States patent (22). The compound produces acute adrenergic cardiovascular responses which are similar to those of dobutamine, but unlike dobutamine, KM-13 is more potent and is effective when administered orally. Several synthetic compounds having uses relating to the cardiovascular system and which can be orally administered were known prior to the disclosure of KM-13 (23, 24, 25, 26).

Because KM-13 is an ionic compound, delivery of the drug by other noninvasive techniques is possible. It has recently been reported that KM-13 can be administered to dogs utilizing an iontophoretic delivery system (27). However, while more potent than dobutamine, KM-13 is not sufficiently potent to be administered to humans iontophoretically, since the current required to deliver an effective dose would cause adverse effects such as skin burns.

Transdermal iontophoresis is a non-invasive technique in which an electrical current is applied to the skin through two electrodes, whereby an ionized drug contained in one of the electrodes moves into the body through the stratum corneum (e.g., skin) in response to the potential across the electrodes. Such a delivery system allows for regulation of the amount of drug absorbed in the bloodstream through the skin as a function of the magnitude of the current applied. Because the system is noninvasive, both trauma and risk of infection are minimized; the later factor has increasing desirability due to the fears generated by the risk of diseases from subcutaneous injections, e.g. AIDS. Transdermal iontophoretic devices have been marketed for several years and are approved by the Food and Drug Administration for use in delivering certain drugs (28). Recently, it has been reported that the beta blocker metoprolol can be delivered iontophoretically (29).

In order for an ESA TM beta agonist system for inducing cardiac stress to be medically practical in both clinical and outpatient settings, there are five criteria that must be fulfilled by the device and the chemical agent used, each of which is met by the invention described and claimed herein: (1) similarity of response to that of exercise-induced stress (the ESA TM beta agonist must elicit cardiovascular responses that mimic the diagnostically revealing responses caused by aerobic exercise); (2) quick onset and cessation of response (as with exercise, the temporal relationship of the heart's response to the ESA TM beta agonist must be a close one); (3) dose related response (as with exercise, the response of the heart to an ESA TM beta agonist must be dose-related such that an increase in the dosage of an ESA TM beta agonist must produce a related increase in the heart's response); (4) safety (the heart's response to an ESA TM beta agonist must be as safe as is the response to exercise); and (5) convenience (there must be a convenient and noninvasive means of delivering the ESA TM beta agonist into the patient). ESA TM beta agonists with beta-1 adrenergic activity are presently preferred, while compounds with beta-2 adrenergic activity can also be useful.

SUMMARY OF THE INVENTION

The present invention is directed to a method of eliciting in a mammal immediate physical responses similar to those physical responses elicited by aerobic activity which comprises administering an exercise simulating agent by a closed-loop drug delivery system. Preferred are exercise simulating agents ("ESA TM beta agonists") having the general chemical structure:

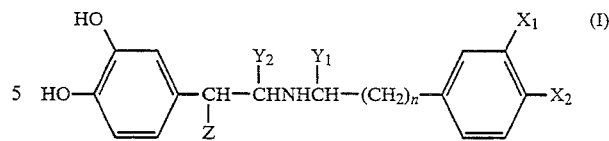

wherein $X_1$ and $X_2$ are independently hydrogen, hydroxy, methoxy or carbamoyl, provided that $X_1$ and $X_2$ are not both hydrogen or carbamoyl; one of $Y_1$ and $Y_2$ is hydrogen and the other is hydrogen or methyl, provided that if $Y_1$ is methyl, then $X_1$ is not carbamoyl; Z is hydrogen or hydroxy; and n is 2 or 3; or a pharmaceutically acceptable acid addition salt thereof.

More preferred are ESA TM beta agonists of the above Structure I wherein Z is hydroxy ("Structure II"). Accordingly, the present invention is also directed to the novel ESA TM beta agonist compounds of Structure II which are more effective at raising heart rate than dobutamine, more potent (on both a molar and a mg/kg basis) than previously known to agents such as KM-13 and dobutamine, and, unlike KM-13 and dobutamine are suitable for administration by non-invasive means such as transdermal iontophoresis. Particularly preferred for diagnostic uses are compounds of Structure II where $X_1$ is hydrogen, $X_2$ is hydroxy or methoxy, and $Y_1$ and $Y_2$ are hydrogen. Preferred are the R-enantiomers and racemic mixtures having the R- and S-enantiomers; of these, the R-enantiomers are most preferred.

According to one aspect of the present invention, there is provided a method of eliciting in a mammal immediate cardiovascular responses similar to those cardiovascular responses elicited by aerobic exercise which comprises: (a) administering an exercise simulating agent (ESA TM beta agonist) to said mammal by a closed loop drug delivery device; (b) controlling infusion of said exercise simulating agent into the bloodstream of said mammal so that a predetermined range of cardiovascular responses is obtained; (c) monitoring the range of responses of said mammal; and (d) changing infusion of said exercise simulating agent as required to maintain said range of responses. Suitable ESA TM beta agonists include compounds of formula I. Preferred ESA TM beta agonists include compounds of Structure II.

According to the above described method of the present invention, in one aspect there is provided a method of simulating the cardiovascular responses of a mammal to an exercise stress test ("ESA TM beta agonist test") wherein the heart of said mammal is exercised or stressed at a selected level without body motion which comprises: (a) administering to said mammal an ESA TM beta agonist having beta adrenergic activity by a closed loop drug delivery device wherein said exercise simulating agent induces reversible myocardial ischemia if CAD is present in said animal and is administered in an amount effective to obtain a preselected range of physical responses in said mammal; (b) controlling infusion of said ESA TM beta agonist into said mammal's bloodstream so as to maintain said preselected range of responses for a preselected time period; and (c) discontinuing infusion of said exercise simulating agent when said preselected time period has expired or when said physical responses are outside said preselected range. Preferred ESA TM beta agonists include compounds of formula I, especially preferred are compounds of Structure II. Two particularly preferred ESA TM beta agonists for diagnostic applications such as the ESA TM beta agonist test described above are those whose preparations are described in Examples 1 and 2 and are termed "ESA TM beta agonist-I" and "ESA TM beta agonist-II" respectively. ESA TM beta agonist-I and ESA TM beta agonist-II exhibit a combination of advantageously high potency and short half-life in the body, making them particularly suitable for use as diagnostic agents. Optionally, infusion of ESA TM beta agonist may be controlled by a power source operatively connected to the mammal which is regulated by a microprocessor connected to both the power source and to an electrocardiographic monitoring device connected to the mammal whereby infusion of said ESA TM beta agonist is feedback controlled by the microprocessor in response to changes in heart rate.

Optionally, the ESA TM beta agonist test method may include, upon discontinuing infusion of the ESA TM beta agonist, simultaneously administering an antagonizing agent having beta adrenergic blocking activity in an amount effective to counteract the physical responses elicited by the ESA TM beta agonist.

Optionally, the ESA TM beta agonist test method may include the additional feature that the flow of electrical current from the power source is discontinued when non-sinus or premature beats of a preprogrammed origin are electrocardiographically detected. Another optional feature of the ESA TM beta agonist test method is that directional flow of electrical current from the power source is reversed upon the occurrence of an event (such as maximal heart rate) preprogrammed in the microprocessor.

The term "closed loop" refers to drug delivery systems in which drug is delivered in automatic response to feedback of a physical signal (or response) which could include responses such as heart rate, blood pressure, ECG, heart output or other similar physical response.

The term "open loop" refers to drug delivery systems in which drug is delivered at a predetermined rate without any direct or automatic adjustment in response to physiological variables.

The closed-loop drug delivery system comprises a system capable of administering precise amounts of drug (ESA TM beta agonist) to the patient so that a desired response level may be maintained or, optionally, increased or decreased. Suitable drug delivery systems include transdermal iontophoretic delivery devices and intravenous delivery devices. The administration of drug by the device may be pulsatile or constant rate. By using pulsatile delivery, it may be possible to deliver less total drug and yet get the same response than with constant delivery of drug.

The closed-loop drug delivery system may include automated blood pressure and electrocardiography devices to allow continuous monitoring of the patient's blood pressure and heart rate during the ESA TM beta agonist exercise test procedure. By monitoring the patient's response to the ESA TM beta agonist, administration of the dose of ESA TM beta agonist may be feedback controlled so that a desired response range is obtained. Moreover, such continuous monitoring of the patient's heart rate and blood pressure, by incorporating various "fail safe" parameters, allows the system to discontinue delivery of the ESA TM beta agonist to the patient or to prevent further cardiovascular activity in response to the ESA TM beta agonist. Thus, the system of the present invention would provide added control and safety to the patient not available during conventional exercise stress testing.

Due to the above-noted features of the closed loop system of the present invention which include (a) automatic feedback control of the administration of the ESA TM beta agonists; (b) suitability for use in the diagnosis of CAD for patients heretofore unable to use exercise stress testing; and (c) incorporation of the above-noted "fail-safe" parameters; the method of the present invention provides a truly safe and efficient system for the diagnosis and treatment of CAD. Many non-conditioned patients do not feel well after an exercise stress test, since they are not accustomed to strenuous physical activity. Such non-conditioned patients who would undergo an ESA TM beta agonist test according to the present invention would not have the adverse muscular effects and exhausted feeling that are often after effects of an exercise stress test.

The ESA TM beta agonist test methods of the present invention may be used in conjunction with other diagnostic tools in order to obtain additional information about a patient's cardiovascular condition. For example, use of the ESA TM beta agonist test in conjunction with diagnostic tools such as echocardiography and radionucleotide imaging would expand the usefulness of those techniques. In the past, exercise echocardiography has been impractical due to technical limitations with the equipment involved which were related to the difficulty of monitoring a moving patient with rapidly expanding lungs and tachycardia. Accordingly, due to its ability to simulate the cardiovascular effects of aerobic exercise without bodily motion, use of the test method of the present invention in conjunction with echocardiography may result in a simulated exercise echocardiography which is clinically practicle. The ESA TM beta agonist test method may also be used in conjunction with radionucleotide imaging using isotopes such as Thallium 201. Since radionucleotide imaging has typically required adequate exercise levels for optimum results, its usefulness for patients unable to exercise adequately or to achieve a maximal heart rate has been severely limited. Use of those techniques in conjunction with the ESA TM beta agonist test method will allow application to clinical situations previously considered unsuitable due to the inability of the patient to exercise or achieve maximal heart rate.

Another aspect of the present invention provides a method of eliciting adaptive cardiovascular and metabolic responses similar to the adaptive and metabolic responses elicited by aerobic activity. One embodiment comprises administration of an ESA TM beta agonist described herein to a patient for a period of from 0.5 to 4.0 hours daily for a period of from 1 to 30 days. This may be accomplished either with or without the iontophoretic delivery device described herein.

A further aspect of the present invention provides a method for increasing cardiac contractility in a mammal having depressed cardiac contractility by administering an effective amount of an ESA TM beta agonist of Structure II. One preferred ESA TM beta agonist is that whose preparation is described in Example 3 herein and which is called "ESA TM beta agonist-III".

The present invention also provides a method of causing adaptive effects in a mammal similar to the adaptive effects caused by aerobic exercise over time which comprises administering an effective amount of an ESA TM beta agonist of Structure II. Particularly preferred are ESA TM beta agonist-I, -II and -III. Due to its longer half-life in the body and enhanced potency, ESA ™ beta agonist-III is particularly suitable for such therapeutic uses.

In an additional aspect, the present invention provides a device for eliciting cardiovascular responses similar to cardiovascular responses elicited by aerobic exercise ("ESA ™ beta agonist device") which comprises: (a) closed loop drug delivery system for administering an ESA ™ beta agonist into the mammal's bloodstream; (b) infusion control system for controlling infusion of the ESA ™ beta agonist into the bloodstream which is operatively connected to the drug delivery system; and (c) monitoring system connected to the mammal to measure a range of responses of the mammal to the ESA ™ beta agonist which is operatively connected to both the drug delivery system and infusion control system such that infusion of ESA ™ beta agonist may be controlled to obtain and maintain a preselected range of responses to the ESA ™ beta agonist. Optionally, the device may include discontinuing system for discontinuing infusion of ESA ™ beta agonist when a preselected time period has expired or when the responses are outside the preselected response range which is connected to the drug delivery system and infusion control system. In the ESA ™ beta agonist device, a microprocessor may be used to regulate the drug delivery system, infusion control system and monitoring system (as well as the optional discontinuing system), and thereby control infusion of ESA ™ beta agonist in response to the measured cardiovascular responses in order to obtain the desired preselected response range. Such ESA ™ beta agonist devices may optionally include a second drug delivery system for administering a beta adrenergic blocking agent which is connected to the discontinuing system and which is activated simultaneously with the discontinuing system. Such ESA ™ beta agonist devices may also optionally include termination system for terminating absorption of the ESA ™ beta agonist into the bloodstream upon activation of the discontinuing system. Suitable termination system include an air-activated tourniquet or occluder cuff.

BRIEF DESCRIPTION OF THE DRAWINGS

FIG. 1 is a block diagram of a closed-loop transdermal iontophoretic delivery system.

FIG. 2 is a logic diagram for the microprocessor software included in the closed-loop transdermal iontophoretic delivery system.

DETAILED DESCRIPTION OF THE INVENTION

Although the method of exercise simulation using closed loop drug delivery of the present invention encompasses the use of various closed loop drug delivery systems including intravenous administration; however, due to its non-invasive nature and concomitant advantages, transdermal iontophoretic delivery is preferred.

In one embodiment of the system of the present invention, precise quantative amounts of a drug can be delivered to the patient by closed loop iontophoretic delivery, and because the amount of drug delivered is controlled by the amount of electrical current needed to move the drug through the skin, delivery of the drug can be readily terminated by either stopping or reversing the supply of current to the electrodes.

Such a closed-loop iontophoretic delivery system of the present invention may utilize microprocessor circuitry to automatically compensate for differences in factors such as skin impedance between patients or even electrode placement on the same patient, or dosages of an ESA ™ beta agonist necessary to achieve the same cardiac response between different patients. This system, by continuously monitoring the cardiovascular effects of the ESA ™ beta agonist via an electrocardiograph, processing the information to determine whether to increase or to decrease ESA ™ beta agonist administration (and therefore heart rate), and then adjusting the amount of current supplied and hence the amount of ESA ™ beta agonist delivered, can efficiently and effectively control the effects of the ESA ™ beta agonist. Such a closed-loop system can safely regulate the amount of ESA ™ beta agonist delivered to the bloodstream of the patient and, thus, allow a predetermined cardiac response to be achieved. Iontophoretic current or electrode impedance can also be monitored.

The transdermal iontophoretic drug delivery device comprises a drug delivery electrode which contains the ESA ™ beta agonist and an indifferent electrode which does not contain the ESA ™ beta agonist and which functions to close the electrical circuit.

The drug delivery electrode for the transdermal iontophoretic delivery device may be constructed according to one of various designs which are known in the art (31, 32, 33, 34, 35, 36, 37, 38, 39, 40). Generally, three types of electrode pads are suitable for use as the drug delivery electrode in the method of the present invention, these being classified as: (1) monolithic pad; (2) reservoir pad; and (3) multilayer pad. Preferred are the monolithic pad and the reservoir pad.

A monolithic electrode pad design provides for including the ESA ™ beta agonist in a polymer that is attached to the electrode. The polymer can also contain an adhesive to maintain contact with the patient's skin. The ESA ™ beta agonist is dispersed in the polymer during manufacture; this material is then formed into the pad itself. An example of a class of polymers suitable for use in such a pad are hydrogels. Preferred hydrogels include poly(hydroxy ethyl methacrylate) (HEMA).

A reservoir electrode pad design allows for addition of the ESA ™ beta agonist drug to an electrode which comprises a disk which is attached to the patient's skin. In such a design, the ESA ™ beta agonist is contained in a reservoir or cavity in the electrode itself. The reservoir or cavity is formed during the manufacture of the electrode. The ESA ™ beta agonist can be added in gel form during manufacture of the pad, after its manufacture, or immediately prior to use.

A multilayer electrode pad includes separate layers for a buffering solution, an ion-exchange membrane and a drug reservoir.

Regardless of the design type of the drug delivery electrode pad, the pad itself may be of any shape, but it should conform to the area of the body where it is applied. The size of the pad may be up to about 20 cm$^2$, but preferably is only as large as required to keep current density below 0.5 mAmp/cm$^2$, since increased pad area reduces current density which may be a major factor in pH change and damage to the patients' skin and build up of a drug depot. If the drug-containing matrix itself has no buffering capacity, the electrode material should comprise a material that undergoes an oxidation reduction reaction. Suitable materials include silver/silver chloride or zinc/zinc chloride electrodes; otherwise a carbon-filled electrode may be used.

The gel may comprise a soluble polyHEMA (hydroxyethylmethacrylate) [Benz Research], hydroxypropylmethyl cellulose [Methocel, ElOM, Dow Chemical] or Carbopol [934P, BF Goodrich] and may include a preservative to prevent microbial growth; parabens, such as methyl, ethyl and propyl, are preferred preservatives. Small amounts of EDTA as a chelating agent may be included. Preferred gels also include an antioxidant to prevent oxidation due to the drug-electrode interaction. Preferred anti-oxidants include sodium bisulfite and vitamin C. The solvent for the gel may comprise deionized, pyrogen-free water or polyethylene glycol (PEG 400, 10–20%). If desired, ethanol (100%) may be added as a cosolvent. The concentration of the drug within the gel is preferably in the range of approximately 5–25 mg/ml gel. It may be desirable to add a small amount of buffer (e.g. citrate, phosphate buffer) to maintain the pH in the electrode.

Prior to placing the drug delivery electrode pad on the skin of the patient, it may be desirable for the technician or doctor to abrade the skin using a clinically acceptable tape material or other method. This removes part of the stratum corneum which is the main barrier to transport of the drug through the skin. Permeation enhancers may be applied topically prior to applying the drug delivery electrode pad to increase the flow of the drug through the skin; preferred permeation enhancers include surfactants such as sodium lauryl sulfate.

Similarly, the indifferent (or return) electrode may be of one of any of the same constructions as the drug delivery electrode except that it contains no ESA TM beta agonist. Since hydroxyl ions may be generated at the site of the indifferent electrode, in order to increase patient tolerance and comfort, and to decrease the occurrence of chemical burns on the patient's skin, it may be preferred for the indifferent electrode to be buffered in order to neutralize ions generated at the electrode site, and to decrease the occurrence of pH elevation.

A typical ESA TM beta agonist test may include several phases: (a) a pre-ESA TM beta agonist monitoring phase; (b) an ESA TM beta agonist delivery phase; and (c) a post-ESA TM beta agonist monitoring phase. In the pre-ESA TM beta agonist monitoring phase, a patient's physical responses are monitored for a period of time prior to beginning administration of the ESA TM beta agonist. This phase allows baseline values for physical responses (such as blood pressure, heart rate, etc.) to be established and allows the patient to become accustomed to the test equipment. Duration of the pre-ESA TM beta agonist monitoring phase is generally at least about ten minutes or longer if additional time is required to establish suitable baseline values. During the ESA TM beta agonist delivery phase, ESA TM beta agonist is administered to the patient according to the administration protocol selected. Administration protocols include ramp protocols, where the ESA TM beta agonist is at a rate to give a continuous, basically linear increase in response (such as heart rate) over time or a step protocol where response is increased in discrete increments and then held at that increased level for a period of time before the next incremental increase. The drug delivery phase lasts until a predetermined point is reached, such as maximum recommended heart rate or an elapsed time period; or it may be ended before completion, for example, if physical responses go beyond a preselected range of response or if an arrythmia occurs. During the post-ESA TM beta agonist phase, the patient is monitored until response values approach the baseline value or until a second predetermined response range (such as heart rate below 100) is reached.

Accordingly, in one aspect, the present invention monitors physiological variables (e.g. heart rate, blood pressure, arrythmia, ischemia, e.g. ST segment deviation) and determines and automatically regulates the administration of ESA TM beta agonists, by means of a closed-loop delivery system consisting of a microprocessor and software operatively connected to a physiological monitoring sensor and a iontophoretic delivery device, said physiological monitoring sensor and iontophoretic delivery device attached to a patient as disclosed in FIG. 1. Referring to FIG. 1, the microprocessor (1) controls the rate of current supplied from the signal driver controller (4), and hence the amount of drug delivered from the drug reservoir located within one of the electrodes (3a) (the other electrode being the indifferent electrode (3b)), to the patient through the transdermal iontophoretic delivery device (3). The amount of current supplied is a function of patient-specific data programmed into the microprocessor by the physician (indicated generally as user interface (5) in FIG. 1) and the response of the patient to the drug, or as a function of the feedback data obtained from the physiological monitoring sensor (2) as predicated upon the particular needs or physical characteristics of a patient relative to the effect of the ESA TM beta agonist upon the patient. For example, the physician may desire a customized protocol whereby the heart of the patient maintains a sustained heart rate of 110 for 3 minutes followed by a heart rate of 120 for 2 minutes, in order to create various levels of stress upon the heart. The specific heart rate and corresponding time thereof can be selected by the physician; the software can be programmed to signal the physician when a predetermined maximum heart rate is approaching. Alternately, the physician may select from a menu any one of several preprogrammed fixed protocols (slow HR rise, moderate HR rise, fast HR rise, etc.) which might be most appropriate for the specific patient. The selected preprogrammed fixed protocol can then be adjusted (if necessary) for the desired maximum heart rate manually by the physician or automatically by the microprocessor.

Additionally, during actual execution of either physician-selected fixed protocols or physician-customized protocols, the system operator may optionally select to HOLD stable at a plateau of a specific HR (not at the maximum heart rate) for a short period of time (potentially several minutes) to enable diagnostic procedures to take place. In this HOLD modality the original protocol is temporarily suspended by the microprocessor and a fixed heart rate maintained (by the closed loop control of administration of the ESA TM beta agonist drug) for the physician's desired time duration. When the HOLD modality is completed (manually indicated by the physician or automatically indicated by the microprocessor) the original protocol may be resumed from the point of suspension or terminated (manually selected by the physician or automatically selected by the microprocessor).

Differences in skin resistivity between patients or even different electrode positions on the same patient can affect the amount of current needed to deliver a given amount of drug iontophoretically. In addition, different patients may also require a different dosage of an ESA ™ beta agonist to achieve the same cardiac response. The present closed-loop system automatically compensates for these differences by continuously monitoring the cardiovascular effect of an ESA ™ beta agonist on a particular patient by way of the sensor, and adjusting the amount of current supplied to the iontophoretic delivery device, and therefore the amount of ESA ™ beta agonist delivered to the patient, will be controlled by the feedback data obtained from the patient's physiological changes or from predetermined data entered into the microprocessor by a physician in accordance with the needs of a particular patient.

In order to monitor the response of the patient to the ESA ™ beta agonist and to ensure his safety, an ECG (heart rate) monitoring device (2a) and a blood pressure monitoring device (2b) are provided to monitor the patient's heart rate and blood pressure. These variables may be prominently displayed on a display screen by the microprocessor. The permeability of the patient's skin for a specific ESA ™ beta agonist, based on skin impedance, can be predetermined and programmed into the microprocessor. Additionally, specific parameters, such as the patient's age, height, weight, sex and other necessary data may be programmed into the microprocessor.

FIG. 2 depicts a logic diagram for a software program which may be used according to one embodiment of the present invention. Using the input variables and the sensor variables, the current necessary to deliver the ESA ™ beta agonist to the patient through the iontophoretic device is calculated; these variables are monitored and are used in the calculation of the ESA ™ beta agonist dose and rate of increase or decrease of ESA ™ beta agonist dose during the course of the study. Following data entry, the key parameters (e.g. blood pressure, heart rate, impedance, and current/dose—mAmp/mMole) are displayed and alarm signals are set which indicate when a specific pre-set level has been achieved. Software within the microprocessor processes the data obtained from the sensor connected to the patient, and based upon those data—as well as the achieving of a selected target heart rate, or the occurrence of some event wherein the physician or patient desires to terminate the delivery of the ESA ™ beta agonist—the control software signals the signal driver controller (4) to either increase, decrease, terminate or reverse the flow of current, and thus the administration of ESA ™ beta agonist.

Current is monitored as another indication of proper functioning of the system, since if too great a deviation from a setpoint current is measured, a problem may have occurred. The control software processes various feedback data obtained from the sensors and functions in increasing, decreasing, terminating or reversing the flow of current to the transdermal iontophoretic delivery device; thus, the amount of ESA ™ beta agonist released from the drug reservoir reflects the processing of such information by the control software. During the study, the entire electrocardiogram tracing can be recorded; electronic storage media can contain the entire study for a specific patient. The information can also be printed on hardcopy by way of a printer attached to the microprocessor. Both serve as permanent records for the patient study.

Once the drug delivery electrode and indifferent electrode are attached to the patient and current flow begins, so that the ESA ™ beta agonist begins to affect the patients' heart rate, the blood pressure and heart rate sensors provide the microprocessor and control software with information so that the current to the iontophoretic device (drug delivery electrode) may be increased or decreased as required to increase or decrease the amount of drug necessary to obtain the desired response (such as heart rate) in the patient.

As indicated in FIG. 1, an ECG amplifier (6), may be connected to the ECG electrodes, to amplify the signal therefrom, which signal is monitored by an R-wave detector (7), which provides the signal driver controller (4) with information on the heart rate of the patient. If the heart rate or blood pressure go beyond a pre-programmed range, or if arrythmia develops, the control software may terminate the flow of current to the iontophoretic device which will immediately terminate delivery of the ESA ™ beta agonist to the patient. Once maximal heart rate is achieved, the flow of current is also automatically terminated. If ischemia is detected, the current flow may be manually or automatically terminated.

The preferred ESA ™ beta agonists used in the method of the present invention advantageously have half-lifes in the bloodstream of a patient of minimal duration. However, an added safety feature may be provided which comprises an optional air-activated tourniquet (8), which can be applied to the patients' body between the iontophoretic device and the heart and which will be manually or automatically activated if heart rate or blood pressure go beyond a pre-programmed range or the development of arrythmia occurs. This feature allows any residual drug to be degraded by ubiquitous enzymes and/or slowly metered into the systemic circulation. Optionally, the microprocessor may be programmed to reverse such flow of current to the iontophoretic device upon the occurrence of the abovenoted conditions which would prevent the ESA ™ beta agonist from entering the bloodstream, as an added safety feature. Reversal of the flow of current would also reverse formation of any drug depot that may develop. Optionally, the method of the present invention may further include co-delivery of an antagonist to the ESA ™ beta agonist, for example, a beta-adrenergic blocker such as propanolol or esmolol, when reversal of the patient's response to the ESA ™ beta agonist is desired to more quickly reverse the effects of the ESA ™ beta agonist on the patient's system.

In another embodiment of the present invention, the closed loop drug delivery device comprises an intravenous ("IV") delivery device. Suitable IV delivery devices include computer controlled IV infusion pumps which maybe controlled by a microprocessor in much the same manner as are the above-described transdermal iontophoretic delivery devices. Suitable IV devices include peristaltic-type, cassette-type, syringe-type, or drop-type apparatus, or any other IV fluid delivery device, and includes devices such as those available from Harvard Apparatus or from IVAC Corp.

Novel ESA ™ Beta Agonist compounds

In one aspect, the present invention is directed to novel ESA ™ beta agonist compounds of the following structure:

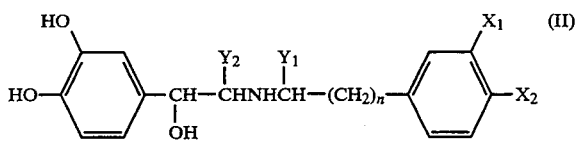

wherein $X_1$ and $X_2$ are independently hydrogen, hydroxy, methoxy or carbamoyl, provided that $X_1$ and $X_2$ are not both hydrogen or carbamoyl; one of $Y_1$ and $Y_2$ is hydrogen and the other is hydrogen or methyl, provided that if $Y_1$ is methyl, then $X_1$ is not carbamoyl; and n is 2 or 3; or a pharmaceutically acceptable acid addition salt thereof. More preferred are compounds wherein $Y_2$ is hydrogen. Especially preferred are compounds wherein $X_1$ is hydrogen.

In particular, due to their advantageous combination of improved potency, on both a molar and a mg/kg basis, compared with agents such as KM-13 and dobutamine, and advantageous half-life in the body, having both an advantageously short onset and cessation of response, the following compounds are especially preferred for use as diagnostic agents according to the present invention:

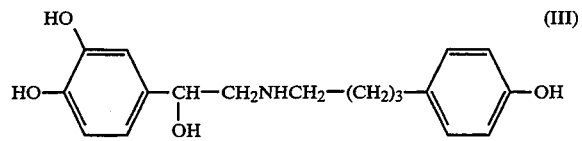

"ESA ™ beta agonist-I"

and

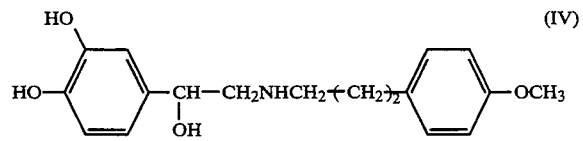

"ESA ™ beta agonist-II"

In particular, ESA ™ beta agonist-I is about 100 times more potent than dobutamine and about 15 times more potent than KM-13 on a molar basis.

Other novel ESA ™ beta agonists of the present invention are particularly suited for use as therapeutic agents due to their advantageous potency coupled with a longer duration of activity. For example, they would be useful as agents for eliciting adaptive cardiovascular and metabolic responses similar to the adaptive and metabolic responses elicited by aerobic activity. One such preferred therapeutic ESA ™ beta agonist comprises the compound of the following formula:

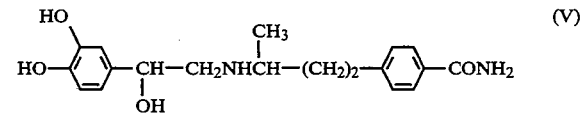

"ESA ™ beta agonist-III"

The novel ESA ™ beta agonist compounds of the present invention may be used as therapeutic agents to take advantage of their therapeutic effects. These effects may be grouped into two general categories: (a) acute and (b) adaptive.

The acute effects refer to the increase of cardiac contractility that occurs while the ESA ™ beta agonist is being administered.

The adaptive effects are those cardiovascular and metabolic responses of the animal provoked by repeated exposure of the animal to the ESA ™ beta agonist. These adaptive responses occur over a time period of weeks. These adaptive responses are similar to those that occur over a time period in response to exercise training over weeks. One principal adaptive response is an increase in the animal's aerobic capacity which improves its exercise tolerance.

Due to their acute effects, these ESA ™ beta agonist would be useful in relieving the symptoms of congestive heart failure.

Due to their adaptive effects, that is, their ability to elicit responses as in exercise training, these ESA ™ beta agonist would be useful in a variety of indications. These ESA ™ beta agonist may be used as a means of rehabilitating patents whose exercise tolerance has been impaired by disease which has forced a period of physical inactivity. Such patients may include those suffering from heart failure caused either by CAD or primary myocardial disease. Other patients who may benefit from such treatment include those whose exercise tolerance has been impaired as a result of peripheral vascular disease, for example intermittent claudication. Another group of patients who would benefit from the adaptive effectives of these ESA ™ beta agonist are those having forced inactivity due to injury; thus, they would be useful in rehabilitating patients who have been confined to bed as a result of injury. These ESA ™ beta agonist would also be useful in treating patients physically incapable of exercise such as paraplegics, quadraplegics, amputees, stroke victims and individuals with advanced arthritis. Another adaptive effect of these ESA ™ beta agonist would be to increase glucose tolerance, for example, in patients with diabetes. Due to the adaptive effects of these ESA ™ beta agonists, they could be used to decrease body fat without losing lean tissue (e.g., muscle) and, thus, could be used in the treatment of obesity and as a means of maintaining and improving exercise tolerance in geriatrics.

These novel ESA ™ beta agonists may be conveniently administered by a variety of routes. Suitable routes of administration include buccal, oral, transdermal passive and transdermal iontophoretic. In particular, ESA ™ beta agonist-III offers advantages over dobutamine as a therapeutic agent in that it is more than 300 times as potent as dobutamine, and exhibits similar effects to dobutamine but does not have to be administered parenterally.

Due to their potency, the ESA ™ beta agonist compounds of the present invention (of which ESA ™ beta agonist-I, -II and -III are exemplary) are particularly suited for administration by transdermal iontophoresis. As noted previously, transdermal iontophoresis offers a non-invasive system for the delivery of diagnostic and therapeutic agents, offering reduced trauma and risk of infection. The latter characteristic has increased desirability due to fears generated by the risk of diseases from IV or subcutaneous injections. However, to be suitable for iontophoretic delivery, the diagnostic or therapeutic agent must have sufficient potency so that an effective dose may be administered at a current level tolerated by the patient. Without use of a buffer in the electrode, use of currents on the order of 1 mAmp/cm$^2$ for an hour will produce a chemical burn. Use of substantial buffer in the drug delivery electrode not only will additionally increase the current required to deliver an effective dose, but may inactivate the agent. Generally, current levels of up to 0.5 mAmp/cm² for 30 minutes may be tolerated without adverse effects such as burns. With agents of sufficient potency, currents as low as about 0.05 mA/cm² or even as low as 0.01 mA/cm² may be used. Preferred current ranges for the ESA TM beta agonists of the present invention are from about 0.1 mAmp/cm² to about 0.5 mAmp/cm². Due to their lower potency, as compared with the novel ESA TM beta agonists of structure II, KM-13 and dobutamine require unacceptably high currents to deliver an effective dose and hence are not suitable for transdermal iontophoretic delivery.

The present invention is directed to the closed loop delivery of ESA TM beta agonists to mammals for the diagnosis, evaluation and treatment of heart disease by a closed-loop system, and includes those novel ESA TM beta agonists disclosed herein, as well as derivatives and salts thereof, as well as other ESA TM beta agonists that accomplish the objectives of the invention. Salts include acid addition salts formed from organic or inorganic acids. Preferred are hydrochloride salts. Other salts include acetate, citrate, hydrogen oxalate, hydrogen tartrate, hydrobromide, and hydrogen sulfate salts, as well as other pharmaceutically acceptable salts.

The Examples that follow demonstrate preparation of some of the novel ESA TM beta agonist's of the present invention (including ESA TM beta agonist-I, -II and -III) by two particular synthetic routes. However, preparation of these ESA TM beta agonist's is not limited to the routes described herein. Other conventional synthetic methods known to those skilled in the art may be used to prepare these ESA TM beta agonist compounds.

Of the two synthetic routes described, the first (See Example 2) comprises coupling a suitably protected bromoketone, such as 3,4-dibenzyloxy-2'-bromoacetophenone with an amine, reducing the resulting amino ketone to the amino alcohol and removing the benzyl-protecting groups.

The second route comprises coupling (R)-norepinphrine with a ketone or aldehyde in the presence of hydrogen and a hydrogenation catalyst, such as a mixture of platinum and palladium catalysts, preferably platinum oxide and palladium on carbon. Use of this second route appears to enhance the yield of the desired product. Also, this route directly allows preparation of the preferred (R)-isomer of the ESA TM beta agonist.

The following examples describe the synthesis of useful exercise stimulating agents. They are set forth for illustrative purposes only and are not to be construed as limiting the claims.

EXAMPLE 1

Preparation of 1-(3,4 dihydroxyphenyl)-2-(4-(4-hydroxyphenyl)-butylamino)ethanol hydrochloride

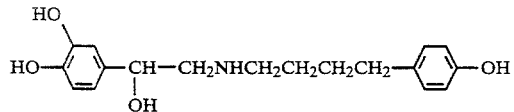

The R-enantiomer is prepared by the procedures described below; some S-enantiomer may be prepared also.

(a) Preparation of 4-(4-Hydroxyphenyl)butanol.

To a solution of 4-(4-methoxyphenyl)butanol (100 g, 0.55 mole) in dichloromethane, cooled to −75° C. in a dry ice-acetone bath, a solution of boron tribromide (278 g; 2.0 mole) was added slowly over one hour. The cooling bath was then removed and the reaction mixture allowed to warm to 15° C. slowly. The reaction was shown to be complete by thin layer chromatography (TLC). The reaction mixture was again cooled in an ice-water bath; 10% sodium hydroxide solution was added until pH of about 9 was obtained. The resulting mixture was then acidified with concentrated HCl to a pH of about 2. The organic layer was separated, the aqueous layer was extracted once with ethyl acetate. The combined organic layers were dried over magnesium sulfate, filtered and concentrated to give 90 g of crude product. The crude product was purified by dry filtration chromatography using 10% ethyl acetate/dichloromethane as eluent giving an 86% yield of pure 4-(4-hydroxyphenyl)butanol. The ¹H NMR was consistent with the assigned structure.

(b) Preparation of 4-(4-Benzyloxyyphenyl)butanol.

To a solution of 4-(4-hydroxyphenyl)butanol (125 g, 0.75 mole) in acetone 0.85.8 g (1.25 mole) anhydrous potassium carbonate (285.8 g, 1.25 mole) was added, followed by 160.8 (0.94 mole) benzyl bromide. The reaction mixture was then heated at reflux for 25 hrs. After cooling to room temperature, the reaction mixture was filtered and the filter cake washed with acetone. The filtrate was concentrated to dryness. The solid residue was washed twice with 500 ml hexane. After drying under high vacuum overnight, 161 g of the desired product were obtained, which was homogeneous on TLC. The ¹H NMR spectrum was consistent with the assigned structure.

(c) Preparation of 4-(4-Benzyloxyphenyl)butanal.

To a solution of 4-(4-benzloxyphenyl)butanol (170.0 g, 0.66 mole) in dichloromethane cooled in an ice-water bath, 215.0 (1.0 mole) pyridinium chlorochromate was added in portions. After the addition was complete, the cooling bath was removed. The reaction mixture was stirred vigorously while warming to room temperature. After 3 hours, the dark brown solution was decanted; 1.5 L of ether was added to the residue. The residue was stirred in ether for 15-30 minutes and then filtered. The organic extracts were combined and filtered through a bed of bentonite. The clear filtrate was dried over magnesium sulfate, filtered and concentrated to afford a near quantitative yield of crude aldehyde (166 g). Purification of the crude aldehyde by dry filtration chromatography using 3% hexane/ethyl acetate as eluent gave 134 g of product. The ¹H NMR spectrum was consistent with the assigned structure.

(d) Preparation of 1-(3,4-Dihydroxyphenyl)-2-(4-(4-hydroxyphenyl)-butylamino)ethanol hydrochloride.

To a 3.8 L pressure vessel, was charged methanol containing 2% acetic acid (2.6 L) and (R)-norepinephrine (44.0 g, 0.26 mole) followed by PtO₂ (5.86 g) and Pd/C (3.9 (g). The mixture was then hydrogenated under 15 psi for 15 minutes. The above butanal (85.9 g 0.34 mole) was added to the mixture and hydrogenation continued at 30 psi for 24–48 hours. The catalysts were removed by filtration. The filtrate was concentrated under reduced pressure to dryness. The crude product was purified by filtration chromatography using dichloromethane/methanol/acetic acid (10:2:0.1) as eluent. The fractions containing the desired product (Rf=0.45, dichloromethane/methanol/acetic acid, 8:2:1) were pooled and concentrated to dryness. The residue (18.0 g) was dissolved in methanol, treated with Dowex 50 X-8 resin and filtered. The filtrate was acidified with concentrated HCl to a pH of about 4, concentrated to a small volume, and then added to anhydrous ether. The desired hydrochloride salt precipitated from the solution, was collected and dried under high vacuum to give 13.5 g of product. Further purification of the fractions containing a mixture of products and Dowex-5 8X treatment gave an additional 12.5 g of slightly less pure product. The first crop of salt was further purified by dissolving in water, filtering and lyophilizing; mp 55°–58° C.; $[\alpha]_D(23°$ C.$)= -18.5$ (C=1.0, $C_2H_5OH$); I.R. 3500, 1600, 1250 CMl; $^1H$ NMR (DMSO-$d_6$) $\delta$8.95 (d,2H,OH), 8.90–8.50 (brd s,2H,NH,OH), 7.00–6.60 (m, 7H, ArH), 6.95 (d,2H, CHOH), 4.75 (m, 1H, CHOH), 3.00–2.90 [m,4H, $CH_2N$], 2.50–2.40 (m,2H,Ar$CH_2$), 1.70–1.50 (m,4H,$CH_2CH_2$).

EXAMPLE 2

Preparation of 1-(3,4-dihydroxyphenyl)-2-[3-(4-methoxyphenyl)-propylamino] ethanol hydrogen oxalate

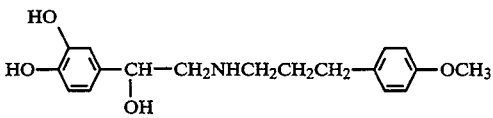

(a) Preparation of N-Benzyl-3-(4-methoxyphenyl) propanamide

To a solution of 10.80 g (0.060 mole) of 3-(4-methoxyphenyl) propanoic acid and 6.57 g (0.065 mole of triethylamine in 25 ml dichloromethane at about 0.5° C., 6.84 g (0.063 mole) of ethyl chloroformate was added dropwise. The mixture was stirred for about 15 minutes at a temperature of about 5° to 10° C., then 6.96 g (0.065 mole) of benzylamine were added. The resulting mixture was stirred for about thirty minutes, and the solvent was evaporated. The residue was slurried in 5% aqueous sodium hydroxide. The solid was collected by filtration and rinsed with water until neutral. The washing process was repeated using 5% hydrochloric acid. The residue was dried under vacuum to give 11.0 g of the above-identified product, melting point 92°–94° C., which was suitable for use in step (b).

(b) Preparation of N-Benzyl-3-(4-methoxyphenyl)-propylamine

To 50 ml of 1M $BH_4$-THF under an argon atmosphere cooled to 0° C., a solution of 4.2 g (0.015 mole) of N-benzyl-3-(4-methoxyphenyl)propanamide in 10 ml anhydrous THF was added. The reaction mixture was stirred overnight, then quenched with water and evaporated. The residue was partitioned in ether and 5% sodium hydroxide. The organic (ether) layer was separated, dried (over $Na_2SO_4$) and evaporated. That residue was dissolved in 50 ml of 10% ethanol in ether; then 2.6 ml of concentrated hydrochloric acid was added. The mixture was stirred overnight. The solid was collected by filtration, rinsed with ether, and dried to give the hydrochloride salt. The free base was obtained by dissolving the salt in a mixture of 10% aqueous potassium carbonate and ether. The ether extract was dried and evaporated to give the 2.8 g of the free base of the above-identified compound. The $^1H$ NMR was consistent with the assigned structure.

(c) Preparation of (R),(S)-1-(3,4-Dibenzyloxyphenyl)-2-[N-benzyl-3-(4-methoxyphenyl)propylamino]ethanol To a solution of 2.04 g (9.0 mmole) N-benzyl-3-(4-methoxyphenyl)propylamine (the product of step (b)) in 20 ml dimethylformamide (DMF), 1.0 g anhydrous potassium carbonate was added. To that stirred mixture, a solution of 3.31 g (8.05 mmole) of 3,4-dibenzyloxy-2'-bromoacetophenone was added dropwise. The resulting mixture was stirred overnight, then poured into water and extracted with methylene chloride, and evaporated. The residue was dissolved in 10% dioxane in ethanol. The solution was cooled to about 0° to 5° C. with stirring, and 2.0 g of $NaBH_4$ were added. The resulting mixture was stirred overnight, then evaporated and partitioned between water and ether. The organic layer was dried (with $Na_2SO_4$) and evaporated under reduced pressure. The residue was chromatographed on silica gel, using chloroform:ethyl acetate. The appropriate (monitored by TLC 95:5 chloroform:methanol) fractions were combined and evaporated. The residue was crystallized from ethanol/ether to give 2.4 g of the above-identified product, melting point 59°–62° C. The $^1H$-NMR was consistent with the assigned structure.

(d) Preparation of (R),(S)-1-(3,4-dihydroxyphenyl)-2-[3-(4-methoxyphenyl)propylamino]ethanol hydrogen oxalate To a solution of 1.50 g (2.6 mmole) of the above benzyl-protected amino alcohol (the product of step (c)) in 150 ml ethanol containing 10% dioxane, 400 mg of 10% Pd on carbon atom were added. The reaction mixture was hydrogenated overnight at 25 psi. To the resulting mixture, a solution of 0.23 g (2.60 m mole) of oxalic acid in 2 ml ethanol was added. After mixing, the solution was filtered and evaporated under reduced pressure. The residue was slurred in ether. The precipitate was collected by filtration, rinsed with ether and then acetone, and dried under vacuum to give 0.570 g of the above-identified product, melting point 158°–162° C. $^1H$ NMR (CD$_3$OD) $\delta$7.0–6.5 (m, 7H, ArH), 4.8 (m, 1H, CHOH), 3.3 (S, 3H, CH$_3$O), 3.00–2.90 (m,4H, CH$_2$N). 2.5–2.4 (m, 2H, ArCH$_2$), 1.6–1.5 (m, 2H, CH$_2$).

EXAMPLE 3

Preparation of 1-(3,4-dihydroxyphenyl)-2-[3-(4-carbamoylphenyl)-1-methylpropylamino]-ethanol acetate and hydrogen tartrate

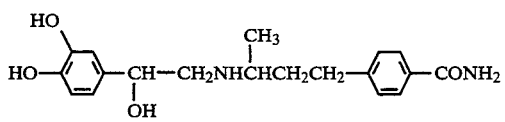

(a) Preparation of 4-(4-cyanophenyl)-2-butone

To a stirred solution of 80.0 g (0.4 mole) of 4-(chloromethyl)benzonitrile and 60.0 g (0.60 mole) of 2,4-pentanedione in 0.5 l of ethanol, 60.7 g (0.44 mole) of potassium carbonate was added. The reaction mixture was then refluxed with stirring for 6 hours. The combined ether extracts were washed with water, dried (with $Na_2SO_4$) and evaporated in vacuo. That residue was distilled. The fraction bpt. 90°–110° C./5 mmHg was recrystallized from ether to give 42.3 g of the above-identified product. The $^1H$ NMR was consistent with the assigned structure.

(b) Preparation of 4-(4-carbamoylphenyl)-2-butanone

To a stirred solution of 9.70 g (0.056) mole of 4-(4-cyanophenyl)-2-butanone (the product of step (a)) in 15 ml of methanol, 1.80 g of potassium bicarbonate and 0.20 g of potassium carbonate were added. To the resulting mixture, 10.0 ml (0.088 mole) of 30% hydrogen peroxide was added dropwise over an hour. The reaction mixture was stirred for 24 hours and then chilled. The solid was collected by filtration, was rinsed twice with water and was dried to give 9.67 g of the above-identified product, melting point 152°–154° C. The $^1$H NMR was consistent with the assigned structure.

(c) Preparation of (R,R),(R,S)-1-(3,4-dihydroxyphenyl-2-[3-(4-carbamoylphenyl)-1-methylpropylamino]ethanol hydrogen tartrate A solution of 3.40 g (R)-norepinephrine and 4.20 g 4-(4-carbamoylphenyl)-2-butanone (the product of step (b)) in methanol containing 2% acetic acid, was hydrogenated over $PtO_2$ and Pd/C at 30 psi as previously described in step (d) of Example 1. After 24 hours the mixture was filtered, evaporated and chromatographed on silica with 4:1:1 chloroform:ethanol:acetic acid. Fractions containing the desired product, as indicated by TLC, were combined, evaporated and dried under vacuum to give the acetate salt as an oil. $^1$H NMR ($CD_3OD$) δ7.5–6.7 (m,8H), 4.7 1 m, 1H, CHOH), 3.3–3.0 (m, 3H, $CH_2N$ and $CH_3CHN$), 2.8–2.5 (m, 4H, $CH_2CH_2$), 2.0 (brd δ, AcO), 1.35 (2d, 6H, $CH_3$). Integration of methyl doublets indicated an R,R:R,S ratio of 53:47.

The hydrogen tartrate salt was prepared by dissolving the acetate salt in methanol and then passing the resulting solution through Dowex 50 X-8 resin. The filtrate was treated with an equimolar amount of tartaric acid, stirred until homogeneous, concentrated and triturated with ether. The solid was collected by filtration and dried under vacuum to give the above-identified product, melting point 85°–90° C.

EXAMPLE 4

Preparation of 1-(3,4-dihydroxyphenyl)-2-[3-(3-carbamoylphenyl)-propylamino]ethanol The compound represented by the following chemical structure:

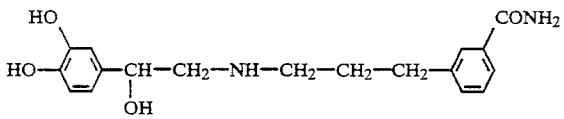

It was prepared according to the following procedure:
(a) Preparation of 3-(3-cyanophenyl)propanoic acid To 200 ml of a solution of 20.0 g potassium carbonate in 250 ml water, 15 g of 3-cyanocinnamic acid was added; the resulting mixture was heated until all the acid was in solution. The solution was cooled and filtered and rinsed with water to 250 ml total volume. Then 0.95 g of 10% palladium on carbon was added and the solution was hydrogenated at 8.5 psi for two hours. The reaction mixture was filtered, and then acidified to a pH of about 1 by the dropwise addition of concentrated hydrochloric acid, being careful to avoid too much foaming. The mixture was chilled in an ice bath and filtered to collect the precipitated product acid. The precipitate was rinsed several times with cold water and dried overnight, to give 13 g of the above-identified product as a solid, melting point 95° C.

(b) Preparation of 3-(3-cyanophenyl)-1-propanol

Into an oven-dried 500 ml flask with 2-neck adapter and stirring bar, 12.9 g of 3-(3-cyanophenyl)propanoic acid (the product of step (a)) was placed. The system was flushed with argon gas; then 84 ml tetrahydrofuran was added. The resulting mixture was stirred until the acid was dissolved. After cooling for about ten minutes with an ice bath, 88 ml borane-tetrahydrofuran was added in two 44 ml portions over a 20 minute period. The reaction mixture was stirred for 20 minutes in an ice bath and then quenched by the addition of about 17 ml water dropwise. The mixture was stripped to give an oil with white crystals. Ether (200 ml) and a solution of 8.8 g (0.22 mole) sodium hydroxide in 150 ml water were added. The organic phase was separated. The aqueous layer was extracted with an additional 35 ml ether. The combined ether extracts were dried over sodium sulfate, filtered, and stripped. The resulting oil was distilled in a Kugelrohr apparatus, the fraction bpt. 95°–110° C. was collected to give 11.5 g of the above-identified product.

(c) Preparation of 3-(3-bromopropyl)cyanobenzene

To a mixture of 21.8 g (0.083 moles) of triphenyl phosphine stirred in 30 ml acetonitrile, 13.2 g (4.26 ml) bromine in 75 ml acetonitrile was added dropwise with stirring in an ice bath. After the addition was complete, the ice bath was removed and the mixture warmed to room temperature. Then a mixture of 12.1 g (0.075 mole) of 3-(3-cyanophenyl)-1-propanol (the product of step (b)) in 30 ml acetonitrile was added dropwise. The resulting mixture was allowed to warm to about 45°–50° C., was stirred overnight and then stripped. Benzene (50 ml) was added to the residue; the mixture was evaporated. Then, additional benzene (50 ml) was added. The mixture was stirred, and then filtered to remove the triphenyl phosphine. The filtrate was stripped to give an oil. The oil was chromatographed using a column containing 3.5 inches of 200 mesh silica gel (Merck) eluting with benzene, until TLC showed that no further product was eluted from the column. The eluates were pooled and stripped to give 17 g of an oil. The oil was distilled in a Kugelrohr apparatus, the fraction bpt. 102°–103° C. was collected to give 15.7 g of the above-identified product as an oil.

(d) Preparation of 3-(3-bromopropyl)benzamide

To 15.2 g (0.067 mole) of 3-(3-bromopropyl)cyanobenzene (the product of step (c)) in 55 ml methanol, 2.2 g potassium bicarbonate was added; to that mixture, 15.2 ml of 30% hydrogen peroxide was added dropwise. The reaction mixture was stirred for about 45 minutes. Then, 113 mg potassium carbonate was added and the resulting mixture was stirred overnight. Water (about 35 ml) was added to the reaction mixture and the resulting solution put in a freezer for about 50 minutes. The solid was collected by filtration and dried overnight to give 15.9 g of the above-identified product as a solid, melting point 109° C.

(e) Preparation of N-[3-(3-carbamoylphenyl)propyl]phthalimide

A mixture of 14.0 g (0.057 mole) 3-(3-bromopropyl)-benzamide (the product of step (d)), 11.5 g potassium phthalimide and 26.3 ml dimethylformamide was heated to reflux under argon gas for four hours. The heat source was removed and the mixture was stirred to cool to room temperature. Water (about 85 ml) was added. The resulting slurry was stirred for 20 minutes, then filtered and washed three times with about 50 ml cold water (each wash made a slurry solution in the funnel). The solids were then washed with about 20 ml cold 1:1 isopropyl alcohol: water and dried under vacuum overnight to give 17.04 g of the above-identified product.

(f) Preparation of 3-(3-aminopropyl)benzamide

A mixture of 15.42 g (0.05 mole) N-[3-(3-carbamoylphenyl)propyl]phthalimide (the product of step (e)), 2.76 g (0.055 mole) hydrazine monohydrate and 100 ml ethanol was refluxed for about four hours under argon with heat, and then allowed to stir overnight. The reaction mixture was acidified with 30% (v/v) hydrochloric acid to a pH of about 1. Additional ethanol (about 10 to 20 ml) was added to the thick mixture. The mixture was filtered; the solids were rinsed with ethanol. The filtrate was evaporated to give a solid. Water (about 15 ml) was added to the solid; the resulting mixture was filtered. The filtrate was basified with dry potassium carbonate until saturated, then extracted three times with 20 ml butanol. The butanol extracts were dried over sodium sulfate and potassium carbonate overnight, filtered and stripped to give 4.25 g of the above-identified product.

(g) Preparation of 3-[3-(benzylamino)propyl]benzamide hydrogen oxalate

To a mixture of 4.25 g (0.023 mole) 3-(B-aminopropyl)benzamide (the product of step (f)) in 55 ml ethanol, 2.79 g (2.67 ml) benzaldehyde was added. The resulting mixture was refluxed for one hour, cooled to room temperature and then filtered. The filtrate was transferred to a Parr bottle containing 222 mg of platinum/carbon 10% (5 ml ethanol was added to wet the catalyst) rinsed with ethanol to a total volume of about 80 ml. After bubbling argon through the solution, it was placed on the Parr at overnight at about 30 psi hydrogen. The mixture was filtered and the solids rinsed with ethanol. The filtrate was stripped to give an oil.

The oil was redissolved in 30 ml ethanol, to that solution 2.14 g oxalic acid in 13 ml ethanol was added dropwise with stirring. The white precipitate that formed was stirred for 25 minutes, then cooled for 25 minutes, filtered to collect the white solids. The solids were slurried with 8 ml cold ethanol and 14 ml acetone, and then dried to give 6.9 g of the above-identified product.

(h) Preparation of 3-[3-(benzylamino)propyl]benzamide (free base)

To 6.7 g (0.0187 mole) of 3-[3-(benzylamino)propyl]benzamide oxalate (the product of step (g)) slurried in 20 ml water, 7.7 g (0.056 mole) potassium carbonate (and 700 mg potassium hydroxide) in 50 ml ethyl acetate was stirred until all solids were dissolved. The aqueous and ethyl acetate phases were separated. The aqueous layer was washed with about 30 ml ethyl acetate. The ethyl acetate extracts were combined, washed over saturated saline and dried over sodium sulfate, filtered. The filtrate was dried to an oil on a vacuum pump overnight to give 4.9 g of the above-identified product.

(i) Preparation of 1-(3,4-dibenzyloxyphenyl)-2-[N-benzyl-3-(3-carbamoylphenyl)propylamine]ethanol To a mixture of 5.00 g (0.018 mole) 3-[3-(benzylamino)propyl]benzamide (the product of step (h)) in 50 ml dimethylformamide (DMF), 3.75 g (0.027 mole) potassium carbonate was added, followed by a dropwise addition of 8.13 g (0.019 mole) 3,4-dibenzyloxy-2′-bromoacetophenone. The reaction mixture was stirred overnight; a drying tube was used. After being stirred for about 20 hours, the reaction mixture was poured into 375 ml water in a 1000 ml separatory funnel. The mixture was extracted three times with chloroform (60 ml, 30 ml and 20 ml respectively). The chloroform extracts were back-washed with a saturated sodium chloride solution, dried over sodium sulfate, and filtered. The filtrate was stripped and pumped under vacuum to give an oil.

The oil was dissolved in 300 ml absolute ethanol. To that mixture, 2.5 g (0.065 mole) sodium borohydride was added; the resulting mixture was stirred overnight (a drying tube was used). The reaction mixture was filtered; the solids were washed with ethanol. The solids were slurried in about 35 to 40 ml absolute ethanol. The slurry was stirred for about 30 minutes in a warm water bath, then cooled in a refrigerator, and filtered. The solids were washed with absolute ethanol and dried under a vacuum pump overnight to give 7.0 g of the above-identified product as a solid, melting point 131° C.

(j) Preparation of 1-(3,4-dihydroxyphenyl)-2-[3-(3-carbamoylphenyl)propylamino]ethanol hydrogen oxalate A 2.0 g portion of 1-(3,4-dibenzyloxyphenyl)-2-[N-benzyl-3-(3-carbamoylphenyl)propylamino]ethanol (the product of step (i)) was recrystallized according to the following procedure: it was dissolved in 15 ml absolute ethanol by heating, then cooled to room temperature and cooled further in a freezer. The solids were collected by filtration, rinsed with ethanol and air dried for 30 minutes. The solids were dissolved in ethyl acetate using heat. The mixture was cooled to room temperature and then cooled in a freezer for about 30 minutes. The solids were collected by filtration and dried under vacuum.

A 0.85 g (1.4 m mole) portion of the recrystallized 1-(3,4-dibenzyloxyphenyl)-2-[N-benzyl-3-(3-carbamoylphenyl)propylamino]ethanol was dissolved in 50 ml methanol with heat. Palladium on carbon (300 mg) was wet with 5 ml methanol in a Parr bottle. The methanol solution was added and rinsed with an additional 10 ml methanol. The mixture was hydrogenated at about 21 to 22.5 psi for about 24 hours. Progress of the reaction was checked using TLC. Argon was passed through the reaction system (to purge the system) while TLC was run. After completion of the reaction, a solution of 126 mg (1.4 m mole) oxalic acid in about 2 ml ethanol was added, and the resulting mixture was stirred for about 10 minutes while passing Argon gas through the reaction mixture. The mixture was filtered and stripped; then about 10 ml methanol was added. To that solution, 10 ml ether was added dropwise (in dry ice). The mixture was put in the freezer overnight. The methanol-ether solution was poured out by pipetting. The solids were washed twice with 50:50 methanol: ether and twice with ether; then dried under vacuum overnight to give about 310 mg of the above-identified oxalate salt.

BIBLIOGRAPHY

1. *Heart Disease: A Textbook of Cardiovascular Medicine.* E. Branwald, Ed "Exercise Stress Testing", T. Shefield, pp. 253–277. W. P. Saunders Co. (1980).
2. Combs et al., "Evaluation of isoproterenol as a method of stress testing." *Am. Heart J.*, 87: 711–715 (1974).
3. Wexler et al., "Electrocardiographic effects of isoprenaline in normal subjects and patients with coronary atherosclerosis." *Br. Heart J.*, 33: 759–764 (1971).
4. Manca et al., "Comparison of Five Different Stress Testing Methods in the ECG Diagnosis of Coronary Artery Disease: Correlation with Coronary Arteriography." *Cardio.*, 64: 325–332 (1979).

5. Kawashima et al., "Noninvasive Demonstration of Underlying Severe Coronary Disease in Patients with Vasospastic Angina," *Clin. Cardiol.,* 10: 329-333 (1987).
6. Tuttle et al., "Dobutamine Conditions the Heart of Dogs with Surgically Narrowed Coronary Arteries," *Am. J Cardiol.,* 39: 298-302 (1977).
7. Berthe et al., "Predicting the Extent and Location of Coronary Artery Disease in Acute Myocardinal Infarction by Echocardiography During Dobutamine Infusion," *Am. J. Cardiol.,* 58: 1167-1172 (1979).
8. Mason et al. "Thallium Scintigraphy During Dobutamine Infusion, " *Am Heart J.,* 107: 481-485 (1984).
9. Mannering et al., "Dobutamine: An alternate Post Infarction Stressor to Exercise Testing," *JACC* 9: 121A (1987).
10. Liang et al., "Conditioning Effects of Chronic Infusions of Dobutamine: Comparison with Exercise Training," *J. Clin. Invest.,* 64: 613-618 (1979).
11. Unverferth et al., "Long-term Benefit of Dobutamine in Patients with Congestive CARDIOMYOPATHY," *Am, Heart J.,* 100: 622-630 (1980).
12. Leier et al., "Diagnosis and Treatment. Drugs Five Years Later—Dobutamine," *Ann. Int. Med.* 99: 490-496 (1983).
13. Leier et al., "Drug-Induced Conditioning in Congestive Heart Failure," *Circulation* 65: 1382-1387 (1982).
14. Liang et al., "Sustained Improvement of Cardiac Function in Patients with Congestive Heart Failure after Shortterm Infusion of Dobutamine." *Circulation* 69: 113-119 (1984).
15. Buttrick, "The Effects of Chronic Dobutamine Treatment on the Normotensive and Hypertensive Heart.: *JACC,* 9: 37A (1987).
16. Sullivan et al., "Prevention of Bederst-Induced Physical Deconditioning by Daily Dobutamine Infusions" "Implications for Drug-Induced Physical Conditioning." *J. Cin, Invest.,* 76: 1632-1642 (1985).
17. Appelled et al., "Intermittent, Continuous Outpatient Dobutamine Infusion in the Management of Congestive Heart Failure." *Am. J. Cardiol.,* 51: 455-458 (1983).
18. Hodgson et al., "Intermittent Ambulatory Dobutamine Infusions for Patients Awaiting Cardiac Transplantation." *Am. J. Cardiol.,* 53: 375-376 (1984).
19. Dies, "Intermittent Dobutamine in Ambulatotry Patients with Chronic Cardiac Failure." *Brit. J, Clin. Prac. Supp.* (oral presentation) 45: 37-39.
20. Roffman, "Intermittent Dobutamine Hydrochloride Infusions in Outpatients with Chronic Congestive Heart Failure." *Clin. Pharm.* 4: 194-199 (1985).
21. Caldwell et al., "Cardiovascular Effects of KM-13, a New, Orally Effective, Cardiotonic Sympathomimetic Amine." *J. Car. Pharmacology* 9: 375-384 (1987).
22. U.S. Pat. No. 4,562,206, entitled "Orally Effective Inotropic Compounds" issued to Tuttle, R. on Dec. 31, 1985.
23. U.S. Pat. No. 3,816,516 entitled "PhenylAlkanulamine, Alkylamine and Alpha-Aminoalky Ketone Derivatives as Heart Stimulants, " issued to Cox et al. on Jun. 11, 1974.
24. U.S. Pat. No. 4,086,272 entitled "PhenylAlkanolamine, Alkylamine and Alpha-Aminoalkyl Ketone Derivatives as Heart Stimulants," issued to Cox et al. on Apr. 25, 1975.
25. U.S. Pat. No. 3,803,230 entitled "5-[2[(1-methyl-3-phenylpropyl)amino]ethyljalicylamide Hydrochloride" issued to Jack et al., on Apr. 9, 1974.
26. U.S. Pat. No. 4,396,627 entitled "Secondary Amines, Their Preparation and Use in Pharmaceutical Compositions," issued to Ainsworth et al. on Aug. 2, 1983.
27. Sanderson et al., "Noninvasive Delivery of a Novel Inotropic Catecholamine: Iontophoretic versus Intravenous Infusions in Dogs." *J. Pharm. Sci.* 76: 215-218 (1987).
28. Tyle, P. "Iontophoretic Devices for Drug Delivery." *Pharmaceutical Research,* Vol. 3, No. 6, 318 (1986).
29. Okabe, et al., "New Iontophoretic Transdermal Administration of the Beta-Blocker Metoprolo." *J. Controlled Release,* 4 (1986) 79-85.
30. U.S. Pat. No. 4,460,689 entitled "Transdermal Drug Applicator and Electrodes Therefor" issued to Sibalis, D. on Feb. 3, 1987.
31. U.S. Pat. No. 4,622,031 entitled "Indicator for Electrophoretic Transcutaneous Drug Delivery Device" issued to Sibalis, D. on Nov. 11, 1986.
32. U.S. Pat. No. 4,557,723 entitled "Applicator for Non-Invasive Transcutaneous Delivery of Medicament" issued to Sibalis, D. on Dec. 10, 1985.
33. U.S. Pat. No. 4,474,450 entitled "Iontophoresis Device" issued to Ariura et al. on Oct. 2, 1984.
34. U.S. Pat. No. 4,340,047 entitled "Iontophoretic Treatment Apparatus" issued to Tapper et al., on Jul. 20, 1982.
35. U.S. Pat. No. 4,325,367 entitled "Iontophoretic Treatment Apparatus" issued to Tapper, R. on Apr. 20, 1987.
36. U.S. Pat. No. 4,250,878 entitled "NonInvasive Chemical Species Delivery Apparatus and Method" issued to Jacobsen et al. on Feb. 17, 1981.
37. U.S. Pat. No. 4,211,222 entitled "Iontophoretic Burn-Protection Method" issued to Tapper, R. on Jul. 8, 1980.
38. U.S. Pat. No. 4,141,354 entitled "Epidermal Iontophoresis Device" issued to Jacobsen et al. on Feb. 27, 1979.
39. U.S. Pat. No. 3,991,755 entitled "Iontophoresis Apparatus for Applying Local Anesthetics" issued to Vernon et al. on Nov. 16, 1976.

We claim:
1. A compound of the formula

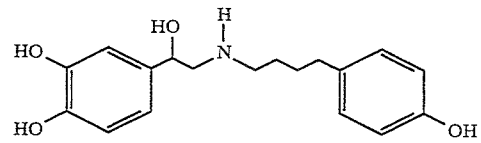

and pharmaceutically acceptable salts thereof.
2. A compound according to claim 1 wherein the pharmaceutically acceptable salt is a hydrogen chloride salt.

* * * * *